United States Patent [19]

van Asselt et al.

[11] Patent Number: 4,671,652

[45] Date of Patent: Jun. 9, 1987

[54] MACHINE FOR CANDLING ARTICLES SUCH AS HATCHING-EGGS

[75] Inventors: Peter A. van Asselt; Jan Hordijk, both of Aalten, Netherlands

[73] Assignee: Staalkat B.V., Aalten, Netherlands

[21] Appl. No.: 790,171

[22] Filed: Oct. 22, 1985

[30] Foreign Application Priority Data

Oct. 22, 1984 [NL] Netherlands .......................... 8403213

[51] Int. Cl.⁴ ............................................. G01N 33/08
[52] U.S. Cl. .......................................... 356/66; 356/53
[58] Field of Search ....................... 356/52, 53, 55, 58, 356/62, 64, 66; 250/223 R

[56] References Cited

U.S. PATENT DOCUMENTS 3,540,824 11/1970 Fonda et al. ............................ 356/53

FOREIGN PATENT DOCUMENTS 2455282 7/1982 France .
0107285 1/1964 Netherlands .

Primary Examiner—Eugene R. LaRoche
Assistant Examiner—Robert J. Pascal
Attorney, Agent, or Firm—Cushman Darby & Cushman

[57] ABSTRACT

A machine for candling articles, such as hatching-eggs, fed on a so-called hatching frame on which the eggs are disposed in juxtaposed rows, which machine comprises a plurality of light measuring systems each including a light source and a sensor. The light measuring systems are arranged in such an array that the articles to be each measured as they rest on the hatching-frame are shielded relative to each other by adjacent articles.

3 Claims, 3 Drawing Figures

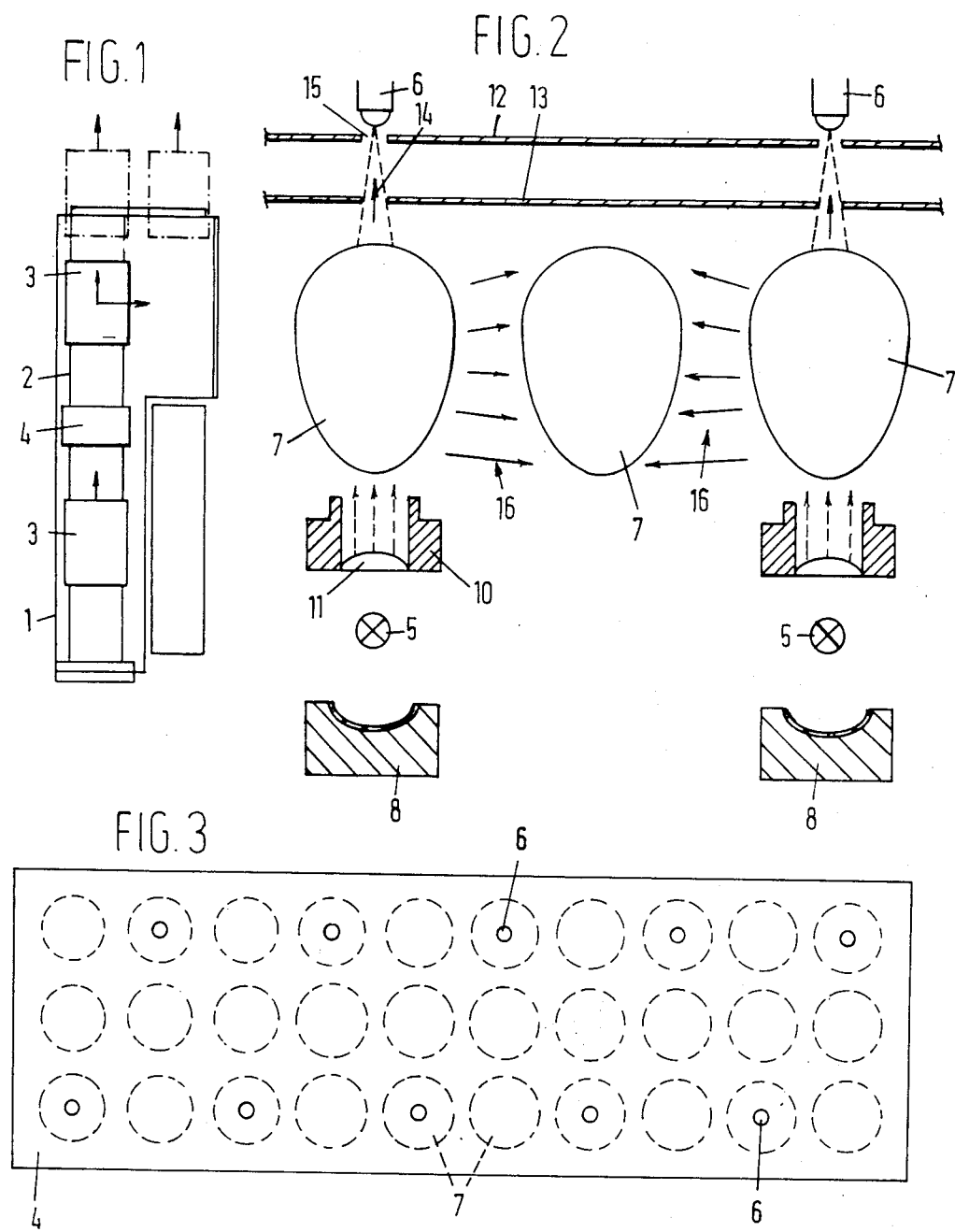

MACHINE FOR CANDLING ARTICLES SUCH AS HATCHING-EGGS

BACKGROUND OF THE INVENTION

The invention relates to a machine for candling articles, such as hatching-eggs, fed on a so-called hatching frame on which the eggs are disposed in juxtaposed rows, which machine comprises a plurality of light measuring systems each including a light source and a sensor, by means of which systems the transmission of light through an egg can be measured: as a fecundated egg absorbs more light than a sterile one, the degree of absorption or transmission is indicative of the fact whether or not the egg is a fecundated one.

In such a prior art machine, which is known from French patent No. 2,455,282, a plurality of eggs disposed beside and behind each other is measured simultaneously. In this prior machine, the light sources are mounted in suction pads to be each time moved towards the article to be measured: this is done to prevent false light and reflection from adjacent eggs from affecting the measurement. Practice has shown that such prevention is insufficient: light emanating from one egg can still reach the sensor associated with an adjacent egg.

SUMMARY OF THE INVENTION

It is an object of the invention to improve the prior art machine.

To this end, in accordance with the invention a machine of the above type is characterized in that the light measuring systems are arranged in such an array that the articles to be each measured as they rest on the hatching-frame are shielded relative to each other by adjacent articles. Consequently, a natural shielding of the articles is used to prevent the measurement from being affected by adjacent articles.

In an embodiment of the invention, the eggs on the hatching frame can be measured during transport thereof, while not in contact with each other, between the light sources and sensors. As there is no contact between the measuring systems and the articles to be measured, i.e., the eggs on the hatching frame, these articles can be transported and measured in a continuous procedure, whereby a high capacity of the machine is achieved.

In another embodiment of the invention, a condenser lens is mounted on one side and a concave mirror is mounted on the other side of each light source, and a diaphragm is mounted on the side of each sensor that faces the light source, which diaphragm comprises two apertured plates mounted in spaced superposition.

The invention will be further explained hereinafter by means of a detailed description of an embodiment of a machine for candling hatching-eggs and with reference to the accompanying drawings, in which:

BRIEF DESCRIPTION OF THE DRAWINGS

FIG. 1 shows a schematic top view of a measuring station provided with the candling machine according to the invention;

FIG. 2 shows a schematic side view of part of the measuring system used in the candling machine shown in FIG. 1; and FIG. 3 shows a schematic top view of the candling machine according to the invention with the relative arrangement of the measuring systems.

DETAILED DESCRIPTION

As shown in FIG. 1, a measuring station 1 is provided with a chain conveyor 2. By means of this conceyor, a hatching frame 3 is fed in the direction indicated by an arrow to a candling machine 4. Downstream of machine 4 the fecundated and the sterile eggs are discharged separately: this is shown in FIG. 1 by means of two chaindotted, juxtaposed hatching frames on the downstream end of measuring station 1.

As appears from FIG. 2, each measuring system essentially comprises a lamp or light source 5 and a sensor 6 spaced such a distance apart that eggs 7 disposed on a hatching frame (not shown) can freely pass therebetween. In accordance with FIG. 2, a concave mirror 8 is mounted below light source 5 and a condenser lens 11 fitted in a housing 10 is mounted above the light source. Two plates 12 and 13 having aligned diaphragm apertures 14 and 15, respectively, are mounted over egg 7 but under sensor 6.

FIG. 3 shows, in a schematic top view of the candling machine, the relative arrangement of the sensors 6 with the light sources 5 vertically therebelow. This Figure shows in broken lines a plurality of eggs 7 disposed in juxtaposed rows on a hatching frame as they are fed through the candling machine. Sensors 6 are shown in full lines. The arrangement makes it clear that the measuring systems 5, 6 are so mounted that there is an article, i.e., an egg, between each two of such systems: on account of this natural shielding, no dispersed light (16 in FIG. 2) from one egg to be measured will be incident upon the sensor associated with another egg to be measured.

A minimum light reflection and hence an accurate measurement is ensured by mounting two spaced-apart plates, which are each provided with a diaphragm aperture, between the article, i.e., the egg, and the sensor.

As the hatching frame supporting the eggs is not in contact with the light sources and sensors during transport, the eggs can be measured while being transported, whereby a high egg handling capacity of the machine is ensured.

It will be clear that numerous modifications of the candling machine according to the invention are feasible without departing from the scope of the invention.

What we claim is:

1. A machine for candling articles, such as hatching-eggs, fed on a hatching frame on which the eggs are disposed in juxtaposed rows, which machine comprises a plurality of light measuring systems each including a light source and a sensor, characterized in that the light measuring systems are arranged in such an array that the articles to be candled as they rest on the hatching-frame are shielded relative to each other by adjacent articles.

2. A machine according to claim 1, characterized in that the eggs on the hatching frame are candled, while out of contact with each other, during the transport between the light sources and sensors.

3. A machine according to claim 1, in which a condenser lens is mounted on one side and a concave mirror is mounted on the other side of each light source, characterized in that a diaphragm is mounted on the side of each sensor that faces the light source, which diaphragm comprises two apertured plates mounted in spaced super-position.

* * * * *